US006709399B1

(12) United States Patent
Shen et al.

(10) Patent No.: US 6,709,399 B1
(45) Date of Patent: Mar. 23, 2004

(54) METHOD AND SYSTEM FOR THE DETECTION OF HEART DISEASE

(75) Inventors: Joseph T Shen, Sands Point, NY (US); Shawn Dentler, Midvale, UT (US)

(73) Assignees: Cardiotran LCC; Premier Hear LLC, Port Washington, NY (US)

( * ) Notice: Subject to any disclaimer, the term of this patent is extended or adjusted under 35 U.S.C. 154(b) by 35 days.

(21) Appl. No.: 09/693,071

(22) Filed: Oct. 20, 2000

(51) Int. Cl.[7] .............................................. A61B 5/0402
(52) U.S. Cl. ...................................... 600/508; 128/923
(58) Field of Search ................................. 128/906, 920, 128/922, 923, 924, 903, 904; 600/508, 509, 513, 515

(56) References Cited

U.S. PATENT DOCUMENTS 5,542,429 A * 8/1996 Feng .......................... 600/515
6,336,900 B1 * 1/2002 Alleckson et al. .......... 128/904

* cited by examiner

Primary Examiner—George R. Evanisko
(74) Attorney, Agent, or Firm—Mitchell A. Stein (57) ABSTRACT

A method and system for the detection of heart disease in a patient, having a remote testing unit for gathering analog data concerning the status of a patient's heart, converting the data to digital form, applying FFT's to the converted data, transferring the data to a computer for analysis. The analytic computer applies mathematical translation to the data received from the remote testing unit into a plurality of different graphical patterns representative of various states of the patient's heart. A data base is also employed that has graphical patterns representative of various states of a plurality of patients' hearts from normal through disease states. The analytic computer compares the graphical patterns of the patient's heart against the data base of graphical patterns recognizes at least one pattern in the data base more similar to the graphical patterns of the patient's heart. The analytic computer then determines a likely diagnosis of the patient's heart as a result of the recognized patterns and outputs the likely diagnosis. Application of Internet and intranet solutions are also provided. A comprehensive data base for storing a wealth of information including clinical data and data acquired is also provided. Firewall protection to maintain confidentiality is included.

16 Claims, 7 Drawing Sheets

METHOD AND SYSTEM FOR THE DETECTION OF HEART DISEASE

FIELD OF THE INVENTION

The present invention relates to the field of multi-phase information analysis applied to the detection and diagnosis of heart disease and more particularly to an Internet or intranet—based system for receiving information concerning a patient and analyzing such information through a plurality of computer resources adapted to apply algorithmic analysis to the information and comparison of the waveform results against a database of known diagnoses to thereby determine the likelihood of heart disease in the patient.

BACKGROUND OF THE INVENTION

Cybernetics theory, utilizing Fast Fourier Transforms ("FFT's), to analyze minute changes in the waveforms of analog signals has been known for years. Application of these theories to EKG outputs is the subject of the book "EKG and EEG Multiphase Information Analysis," written by Prof. Genquan Feng, and copyrighted in 1992, the contents of which are incorporated by reference ("Professor's Book") EMPI technology, as disclosed in Professor's Book represents a novel way of analyzing EKG and EEG signals through use of FFT's.

Also known are systems that employ EMPI technology, as shown in the following U.S. Patent which are co-licensed U.S. Pat. Nos. 5,649,544; 5,542,429; 5,533,522; 5,509,425. None of these patents, however, teach an Intranet or intranet solution involving remote data gathering and analysis of information. While U.S. Pat. No. 5,421,343, also co-licensed, discloses certain aspects of remote data acquisition, it fails to account for the division of activities and information flow between multiple computers, data base configurations, firewalls, or other aspect of a complete solution for detection of heart disease.

Additionally, EKG information is but one form of information that can be acquired about a patient's condition and health, and hence it is heretofore unknown to acquire information from a clinical questionnaire, audio pickups (showing audible heart information) and video images of patients in a comprehensive manner which, when added to EMPI, provides more accurate diagnostic ability.

It is thus an object of the instant invention to provide an Internet (or intranet)—based solution to enable remote data collection of heart-related information (EKG, audio, patient information and video images), initial analysis, and transmission via the Internet (or intranet) to a server where diagnoses in accordance with EMPI process steps can occur and reports are generated, and further involving a comprehensive database, including patient data collected via a clinical questionnaire and video images of patient, all as described and achieved hereinbelow.

SUMMARY OF THE INVENTION

The various features of novelty which characterize the invention are pointed out with particularity in the claims annexed to and forming a part of the disclosure. For a better understanding of the invention, its operating advantages, and specific objects attained by its use, reference should be had to the drawings and descriptive matter in which there are illustrated and described preferred embodiments of the invention.

The foregoing objects and other objects of the invention are achieved through a method and system for the detection of heart disease in a patient, having a remote testing unit for gathering analog data concerning the status of a patient's heart, converting the data to digital form, applying FFT's to the converted data, transferring the data to a computer for analysis. The analytic computer applies mathematical translation to the data received from the remote testing unit into a plurality of different graphical patterns representative of various states of the patient's heart. A data base is also employed that has graphical patterns representative of various states of a plurality of patients' hearts from normal through disease states. The analytic computer compares the graphical patterns of the patient's heart against the data base of graphical patterns recognizes at least one pattern in the data base more similar to the graphical patterns of the patient's heart. The analytic computer then determines a likely diagnosis of the patient's heart as a result of the recognized patterns and outputs the likely diagnosis. Application of Internet and intranet solutions are also provided. A comprehensive data base for storing a wealth of information including clinical data and data acquired is also provided. Firewall protection to maintain confidentiality is included.

Other features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In in the drawings, wherein similar reference characters denote similar elements through the several views.

DETAILED DESCRIPTION OF THE PREFERRED EMBODIMENTS

Figure 1:
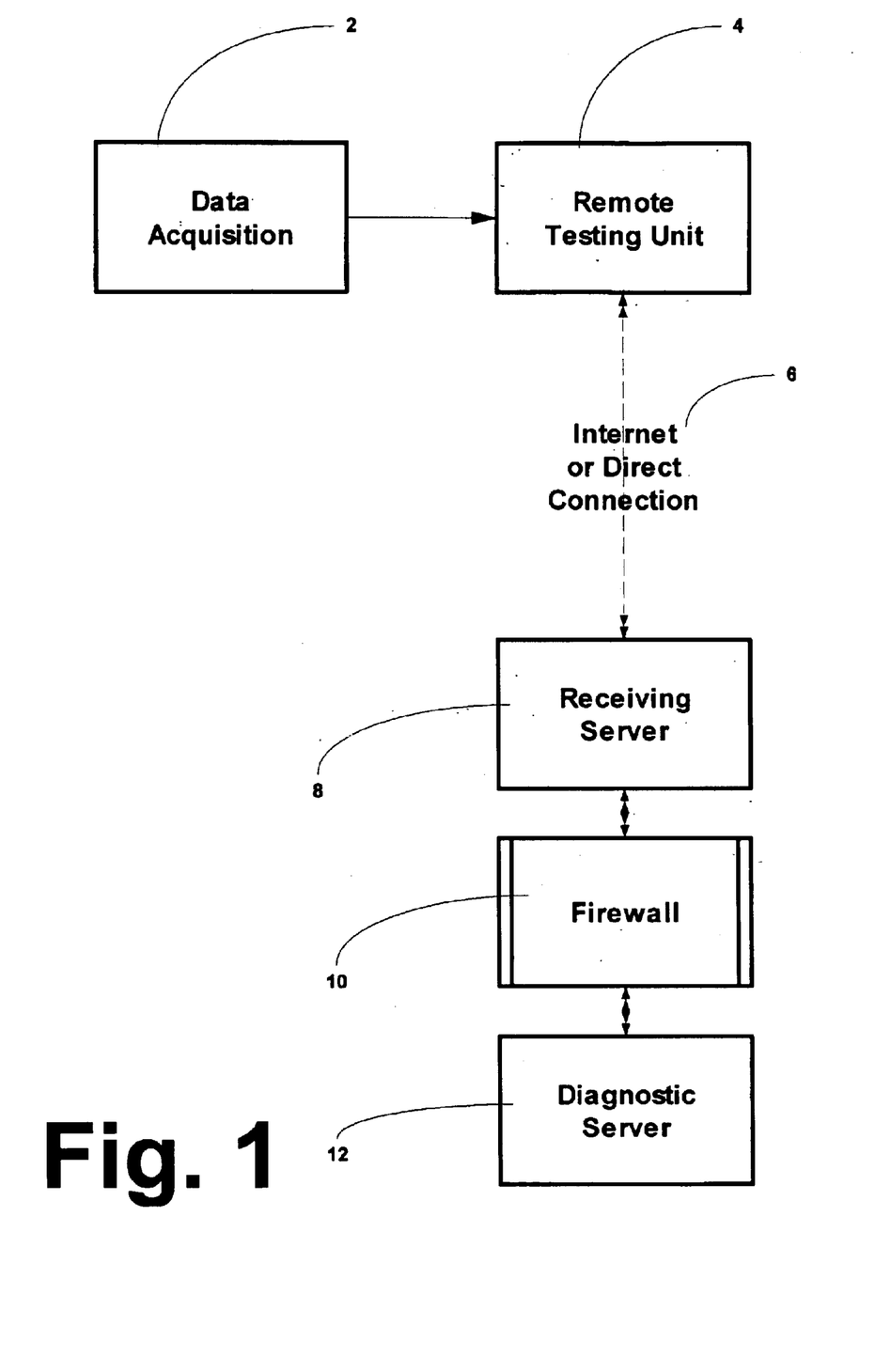
FIG. 1 is a general systems overview diagram.

In accordance with the subject invention, FIG. 1 shows the major components of the preferred embodiment for the acquisition of data, initial analysis, and the transmission to the various servers for provision of diagnoses and reports. Initially, data in a number of different forms is acquired by data acquisition step 2 from a plurality of sources including patient information, EKG leads, audio pickups for audio heart data and video images, as shown in greater detail in FIG. 2 and described in connection with that figure, below.

Returning to FIG. 1, after data is acquired via step 2, remote testing unit 4 receives the acquired data. Remote testing unit 4 is a computer responsible for hosting the data acquisition and initial analysis software and hardware, storing the acquired data, performing a series of mathematical EMPI conversions, and initiating, managing, and confirming the transmission of the converted data to receiving server 8. In accordance with a preferred embodiment of the invention, remote testing unit 4 is an IBM—compatible personal computer with a suitable operating system, currently a 32-bit system running either Windows 95, Windows 98, Windows NT 4.0, or Windows 2000. Remote testing unit 4 further comprises a communication device for transmitting and receiving data, as well as a monitor, and operator control through a mouse, keyboard, or other control mechanism.

Data acquisition step 2 involves the acquisition of data from a plurality of sources, and thus the specific configuration remote testing unit 4 can be modified in accordance with the parameters of that acquisition. For example, where the physician seeking to acquire the necessary data is in an environment that does not permit easy attachment to power, or for any other reason, a notebook computer can be used for the remote testing unit 4. Wearable computers that also run on battery power can be used, as well. Where the doctor has the facilities to accommodate a larger unit 4, then a full-size computer can be employed. All that is necessary for remote testing unit 4 is that it be capable of receiving the data via data acquisition step 4, performing certain FMPI data analysis as described in greater detail below, and transmitting the data to receiving server 8 via Internet or a direct connection through step 6. In certain instances, remote testing unit 4 will also receive diagnoses and reports from diagnostic server 12 through firewall 10 to receiving server 8 and via the Internet or direct connection step 6, in order to provide such diagnoses and reports to the physician. In other instances, the reports and diagnoses are provided in other manners, as described further below. In those instances in which remote testing unit 4 must accommodate the presentation of diagnoses and reports, a report generator (any typical printer will do) is further included. Other necessary or beneficial components for remote testing unit 4 will become apparent to one of ordinary skill in the art upon consideration of the fill functionality as described herein below.

After acquiring data via step 2, remote testing unit 4 performs certain EMPI functions and transmits modified, acquired data via the Internet or by away of a direct connection through step 6 to a receiving server 8. It should be appreciated that although the Internet is a preferred mechanism for transmitting data, a direct connection or intranet NIC card connection can also be employed. A direct connection can involve a direct dial-in to the receiving server 8 via modem or a local area network. Remote testing unit 4 thus includes a modem, in the preferred embodiment, capable of dialing into a corresponding and compatible modem on receiving server 8, when a direct connection is used. When an Internet—based connection is used, the remote testing unit 4 includes a modem capable of dialing into an Internet Service Provider which will route the call to receiving server 8. In an alternative embodiment, a network interface card is provided in remote testing unit 4 that is capable of communicating with a compatible network interface card on receiving server 8 that is on the same local area network as the remote testing unit 4. Likewise, a network interface card can be used that is capable of establishing a connection to a proxy (a proxy—serving computer or a proxy device such as an asynchronous digital subscriber modem), which proxy then establishes a connection to receiving server 8 via the Internet.

In operation, there will be a plurality of remote testing units 4 that will, at any given time, engage receiving server 8. This is because more than one physician will be seeking to diagnosis a patient at any given time, and will engage a remote testing unit 4 to acquire the necessary data via step 2, perform initial data analyses, and forward that data via step 6 to the receiving server 8. Thus, receiving server 8 accepts connections from the plurality of remote testing units 4, and downloads data from them, as well as making available for upload any required information through the same channels, in those instances in which the diagnoses and reports will be provided at the remote testing unit 4. Also, receiving server 8 logs and backups the data, and then directs the received data via firewall 10 to diagnostic server 12. Reports received back by the receiving server 8, as discussed in greater detail below, are also made available to remote testing units 4, or otherwise transmitted (e..g., via e-mail or other) to the physician for reporting purposes.

Currently, receiving server 8 comprises an IBM-compatible personal computer (PC) with a server-oriented operating system (OS) such as Windows NT 4.0, Windows 2000, or any of the varieties of Linux and Unix OS' currently available. As with the remote testing unit 4, receiving server 8 includes a monitor, as well as a control mechanism for inputting commands, currently a mouse and keyboard compatible with the selected OS. Receiving server 8 also includes at least one communication device capable of connecting and transmitting data from the plurality of remote testing units 4 via the Internet or direct connection step 6. Accordingly, such communications devices may include a modem or array of modems. Alternatively, a network interface card that is capable of achieving communications with other devices on a local area network can be employed. Likewise, the network interface card can be used that establishes a connection to a proxy (a proxy-serving computer or a proxy device such as an asynchronous digital subscriber [ADSL] modem or a frame-relay system), which proxy must be capable of accepting connections from remote testing units 4 Via the Internet. Critical to the communication devices selected is compatibility between the receiving server 8 and the plurality of remote testing units 4.

Receiving server 8 also comprises sufficiently substantial data storage means, currently a hard drive or hard drives on which to store the data received from the plurality of remote testing units 4, the size of which is proportional to the quantity of remote testing units 4 that subscribe to the system and the duration of time in which their data must reside actively on the receiving server 8. This hard drive must be dependable and resistant to faults or loss of data due to drive failure, preferably by being composed of a redundant array of independent disks (RAID) or other then available state of the art data storage devices The server must also have a removable storage drive of sufficient capacity to store all data in compressed form, such as a high-capacity DAT drive or a CD-R drive. The data must be backed-up to this removable medium with a regular and reasonable periodicity in order to minimize loss of data due to a physical catastrophe or an unrecoverable system crash. Hot swapable, mirrored drives can also be employed.

In operation, receiving server 8 establishes a connection with the corresponding remote testing unit 4. This consists of awaiting a request for connection, and then, when a request is received, authenticating the remote testing unit 4 and responding with a positive message if the connection and authentication are successful. The receiving server 8 facilitates more than one "client" connection simultaneously, i.e. more than one remote testing unit 4, the specific capacity dependent upon the maximum observed user load at peak times. The software necessary to complete this task can be native services offered by the OS, such as the file transfer protocol (FTP), a custom-developed piece of software such as a service that transmits data via a TCP/IP connection with the client, or it can be an existing software package, such as Microsoft SQL Server. Whichever data method software package is selected, the software resident in the remote testing unit 4 must be compatible.

Secondly, the receiving server 8 must log and back up the raw data, both for auditing purposes and to guard against loss of data due to failure in the course of its processing. Prior to this, it may be necessary to decrypt the data if the data was transmitted in encrypted form instead of having used a secure channel. In the preferred embodiment, encryption algorithms are employed. To store the data, data storage software is used. This takes the form of either a database system, such as Microsoft SQL Server or an Oracle system, or a file-based system in which all data is stored in discrete files that are indexed or organized in a predetermined fashion.

Thirdly, receiving server 8 exports the initially analyzed data received from the remote testing units 4 through firewall 10 to diagnostic server 12 for processing. In certain instances, this transfer involves authenticating and authorizing the data before its transmission. This transfer occurs in accordance with the nature of firewall 10, as described below.

Fourthly, receiving server 8 reincorporates the processed data from diagnostic server 12 by importing that data through firewall 10.

Fifthly, receiving server 8 renders the processed data available for generating diagnoses and reports to be reviewed by the physician. There are a number of different manners in which the instant invention provides reports to the physician or ordering practitioner. The reports can be sent back to the remote testing unit 4 that is responsible for having forwarded the data (in order for the report to conform with the particular patient whose data was sent). Otherwise the reports are generated and forwarded to the practitioner.

Reports are also generated either upon demand or automatically. When reports are generated automatically upon completion of the analyses, receiving server 8 generates the report using a reporting engine such as Seagate Crystal Reports and then forward that report to the practitioner through either electronic mail as an attachment, facsimile, or other known means including, e.g., an overnight or other courier, or express postal mail. When the report is generated on demand, receiving server 8 will await a request from the ordering physician for the report, and, when requested, create the report as a file using a reporting engine or as a hypertext markup language (HIML) document. In the case of the report being a generated file, the file is rendered available for download via FTP. In the case of the report being an HTML document, it is presented to the practitioner through a Web server to the practitioner's Web browser, such as Microsoft Internet Explorer (MSIE) or Netscape Navigator (NS), or other then available Internet Web software.

It should be now observable that the process steps are divided between remote testing unit 4, receiving server 8 and diagnostic server 12. Generally, remote testing unit 4 is responsible for initial analyses, and then for forwarding that initially analyzed data to receiving server 8. Diagnostic server 12 performs the detailed EMPI calculations upon the data that it receives from the receiving server, and then forwards the results to the receiving server 8 which stores the results for later review by the practitioner, and which generates reports of those results.

The specific component conformation shown in FIG. 1 provides protection against infiltration and corruption of software and data, necessary not only to protect the specific code and process steps that each of the devices provides, but to ensure that patient data cannot be obtained without authorization. In particular, firewall 10 insulates diagnostic server 12 from the Internet in order to keep secure the intellectual property manifested thereon, maintain the confidentiality of all patient data, and to protect the hardware and software from malicious damage. In one embodiment, firewall 10 possesses both a software, or automated, component, and a human, or methodological, component. The automated component allows only authorized and authenticated undiagnosed patient data to flow from the external world through it and only authorized and authenticated diagnosed patient data to flow back through it. A properly configured Microsoft Proxy Server is one example.

An actual air gap that is manually administered is the most extreme example of firewall 10, manifesting itself completely as a methodological firewall. The methodological firewall involves properly securing all passwords and other credentials and also securing the facilities in which the diagnostic and receiving servers reside. In this embodiment, the data from receiving server 8 is actually downloaded to a removable medium (floppy, CDROM, DAT, or other), removed from receiving server 8, carried by hand to diagnostic server 12, and then read by diagnostic server 12. Diagnostic server 12 then performs its analyses, exports the data back to the removable medium, whereupon it is carried again by hand to receiving server 8 for generating reports to the ordering practitioner. In this manner, preservation of the integrity of diagnostic server 12 is achieved. It should be appreciated that other, less severe mechanisms can be employed depending upon the degree of assurance that is required.

Diagnostic server 12 performs the analyses that are described in greater detail herein below. Diagnostic server 12 must be capable of performing these mathematical analyses for a multiplicity of patients, simultaneously, thereby minimizing the lag time between data acquisition step 2 and the generation of reports. Accordingly, diagnostic server 12 is preferably a minicomputer with parallel processing ability or a larger system. (Add greater detail here.)

Figure 2:
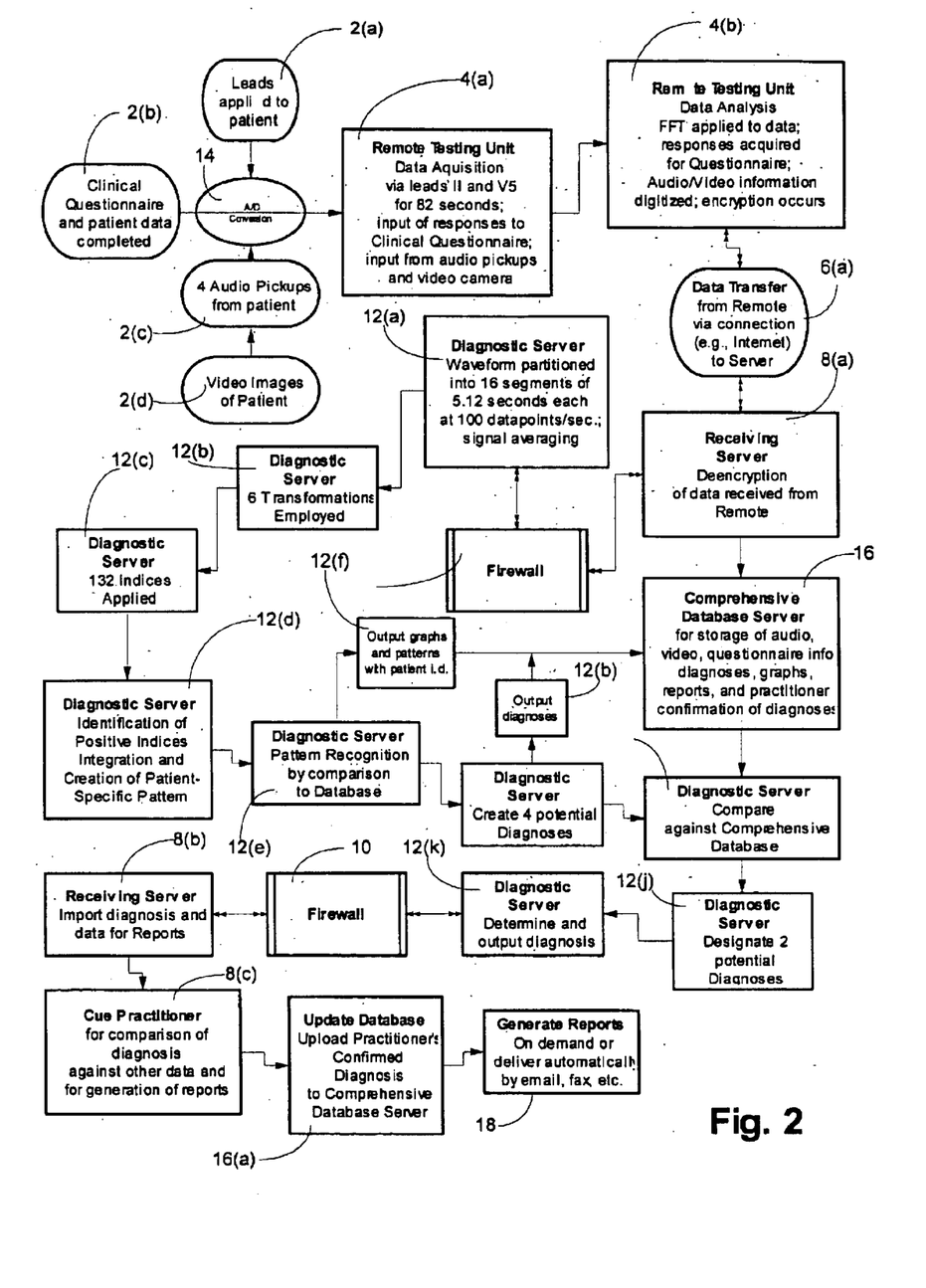
FIG. 2 is a detailed overview diagram of a preferred embodiment.

FIG. 2 shows the components of the preferred embodiment in greater detail. In particular, EKG leads are applied to the patient via step 2(*a*) at lead II and V5, in accordance with generally recognized locations for these leads. Because these leads pickup analog information, this information must be amplified and digitized via A/D conversion at step 14. In this manner, EKG information can be supplied to remote testing unit 4 at step 4(*a*). In the current preferred embodiment, data is acquired by step 4(*a*) through remote testing unit 4 by receiving analog information digitized by step 14, leads II and V5 for a period of 82 seconds. Other sampling rates may be employed, however, this period of time is required for EMPI analysis in accordance with the techniques stated in Professor Feng's book (herein before defined) and Patents (herein before defined and co-licensed).

This invention further comprises the addition of a clinical questionnaire in which patient data is acquired at step 2(*b*). Such information may be provided in written form, and then digitized via step 14, or by way of software prompting by which the information is provided in computer—viable form, thereby not requiring conversion. In the typical EMPI analysis, patient data is not acquired and compared against the results of the analysis. The purpose of the acquisition of such information is to provide further ability to refine the diagnosis and thereby improve the accuracy. The information obtained at step 2(*b*) includes clinical information received from the patient and relating to any present illness, a full systems review, past medical history, past surgical history, current medication, and social history.

EMPI analysis does not include the receipt and analysis of audio information obtained from listening to the heart other than that which is obtained via EKG leads II and V5. As a result, audio information indicative of heart activity but not received via EKG is ordinarily lost. In the instant invention, 4 audio pickups are placed at locations on the patient's body at step 2(*c*). The output from the audio pickups is digitized at step 14 and received via remote testing unit 4 at step 4(*a*).

Traditionally,. physicians diagnose patients by "seeing" them. Accordingly, when a physician examines the patient, the patient is in viewing distance of the physician. In order to emulate that typical environment, video images are procured via step 2(*d*). Thus, when a patient is submitting to the diagnostic examination in accordance with the subject invention, the patient is videographed during the examination. This also provides the ability to confirm patient identity for billing purposes.

Thus, the instant invention provides receipt of EKG information via step 2(*a*), clinical questionnaire and patient data via step 2(*b*), audio information of the heartbeat via step 2(*c*), and video images of the patient via step 2(*d*). This information is acquired by remote testing unit 4 and eventually stored in comprehensive database server 16. The practitioner can access the patient's entire file, including all the acquired information, for recall, verification and further diagnostic analysis.

After the data is acquired by a remote testing unit 4 at step 4(*a*), the data is initially analyzed by remote testing unit 4 at step 4(*b*). Fast Fourier Transforms ("FFT's") are applied to the EKG data in accordance with EMPI process steps. The remaining data acquired in steps 2(*b*), 2(*c*), and 2(*d*) are gathered in digital form with the EKG data transformed by the FFT's, and this patient—specific data is encrypted in process step 4(*b*). After encryption, the data is transferred from remote testing unit 4 via data transfer step 6(*a*) to receiving server 8, where de-encryption occurs at step 8(*a*). Alternatively, the data can be communicated over a secure, encrypted channel Pre-communication data encryption should preferably be done with an RCA algorithm, which has the additional benefit of guaranteeing the identity of the sender, or client. Secure communication can be performed using any version of the point-to-point tunneling protocol (PPTP), preferably Microsoft virtual private networking (VPN), which is natively and easily supported by the predetermined Microsoft OS. Failures in communication are recognized in handled between remote testing unit 4 and receiving server 8. Any incomplete or corrupt data is automatically recognized as such and discarded, preferably with a log record maintained. Remote testing unit 4 notes the data that has not been successfully transmitted, re-transmits that data when the opportunity is given, and displays a descriptive error message. Encryption is provided at this point to insure that information transferred between remote testing unit 4 and receiving server 8 is not hacked.

After receiving server 8 receives and de-encrypts the data via step 8(*a*), the EKG data is passed through firewall 10 to the diagnostic server 12. Diagnostic server 12 then performs a number of EMPI mathematical computations on the EKG data, in accordance with Professor Feng's Book and Patents. In particular, the EKG data waveform is partitioned into 16 segments of 5.12 seconds each at 100 datapoints/second, and the signals are averaged, via step 12(*a*). Diagnostic server 12 then performs the six transformations at step 12(*b*), applies the 132 indexes at step 12(*c*), identifies positive indices and integrates and creates a patient-specific pattern at step 12(*d*). At step 12(*e*), the patient-specific pattern is compared against that of a database that contains a number of patterns including various heart disease states, as well as disease-free states, and by employing known pattern recognition modalities, determines which of the database patterns are the closest fit. Four potential diagnoses are identified via step 12(*g*). Meanwhile, the patient-specific patterns are exported via step 12(*f*) to the comprehensive database 16 to be stored with all of the other patient-specific data. Likewise, the four potential diagnoses are also output via step 12(*h*) to the comprehensive database server 16. Then, at step 12(*i*), diagnostic server 12 compares the four potential diagnoses against the other patient-specific data provided by comprehensive database server 16 in order to narrow the four potential diagnoses down to two. These diagnoses are then determined and output at step 12(*k*). This output is passed through firewall 10 back to receiving server 8, and is imported for generation of the diagnosis and reports at step 8(*b*).

Once the diagnosis and reports are complete, in a preferred embodiment shown in FIG. 2, the practitioner is cued at step 8(*c*) for comparison of the diagnosis against other data that the practitioner may have maintained, and for generation of reports. After the diagnosis is confirmed (or modified) by the practitioner at step 16(*a*), reports are generated via step 18. As stated before, these reports may be delivered automatically via data transfer 6(*a*) to remote testing unit 4, or can be sent via e-mail, fax or other known means.

It should be recognized that the reports generated by the instant invention comprise detailed analyses of, and provision of waveforms, together with diagnoses gleaned from those waveforms and by pattern comparison against the database. Also included are patient-information received from the clinical questionnaire, and available are the audio information and video images, also received via the invention.

Figure 3:
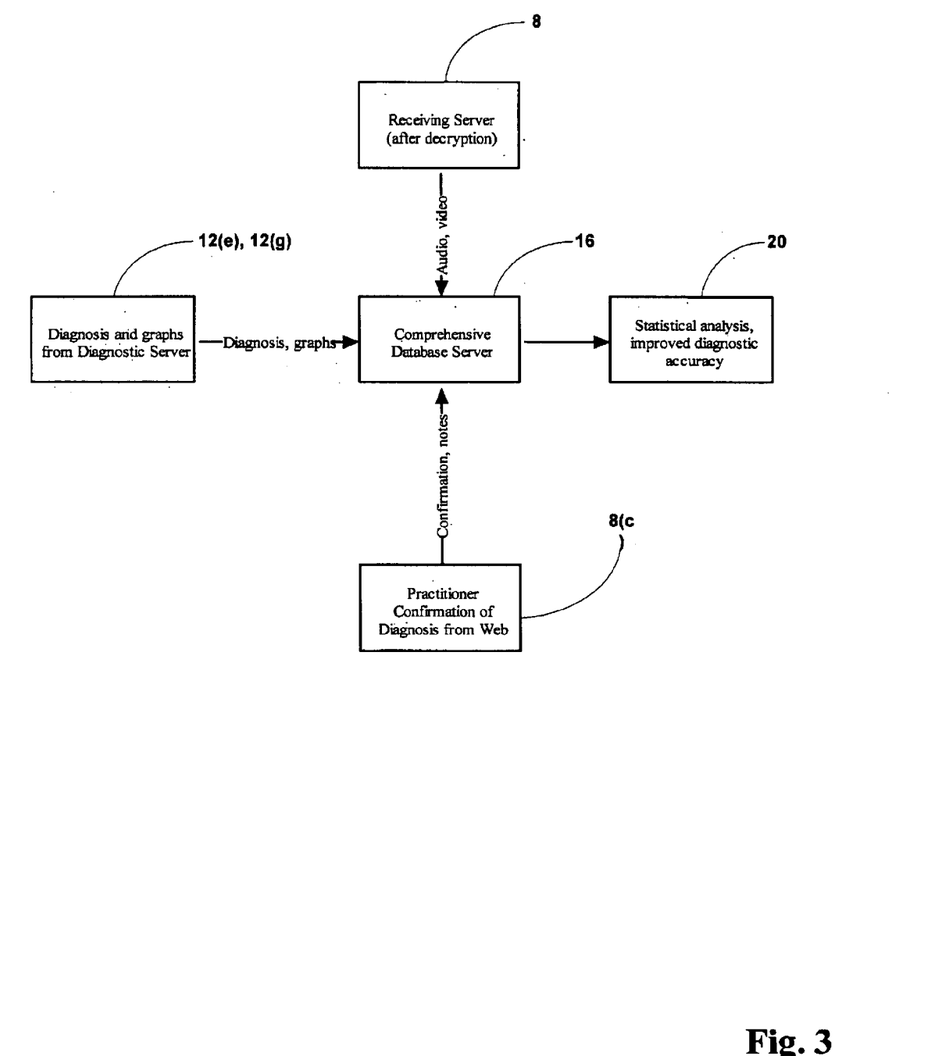
FIG. 3 is a diagrammatical representation of the interaction between the components of the comprehensive database server.

FIG. 3 shows further detail of the comprehensive database server 16 which maintains a wealth of patient-specific information. In particular, diagnosis and graphs from diagnostic server 12 are passed via steps 12(*e*) and 12(*g*) to comprehensive database server. Also, audio and video information received by receiving server 8, after decryption, are also imported to comprehensive database server 16. Lastly, practitioner confirmation (or modification) of the diagnosis, received via the Internet or direct connection at step 8(*c*) are imported to the comprehensive database server 16. As a result, comprehensive database server 16 is then capable of applying statistical and other analysis to improve the accuracy of the diagnoses provided. Moreover, because comprehensive database server 16 maintains not just the EMPI information but audio, video, clinical questionnaire and practitioner-supplied information, it has a greater capacity for comparisons to be applied to new patients, thereby providing further ability to refine new patient diagnoses.

Figure 4:
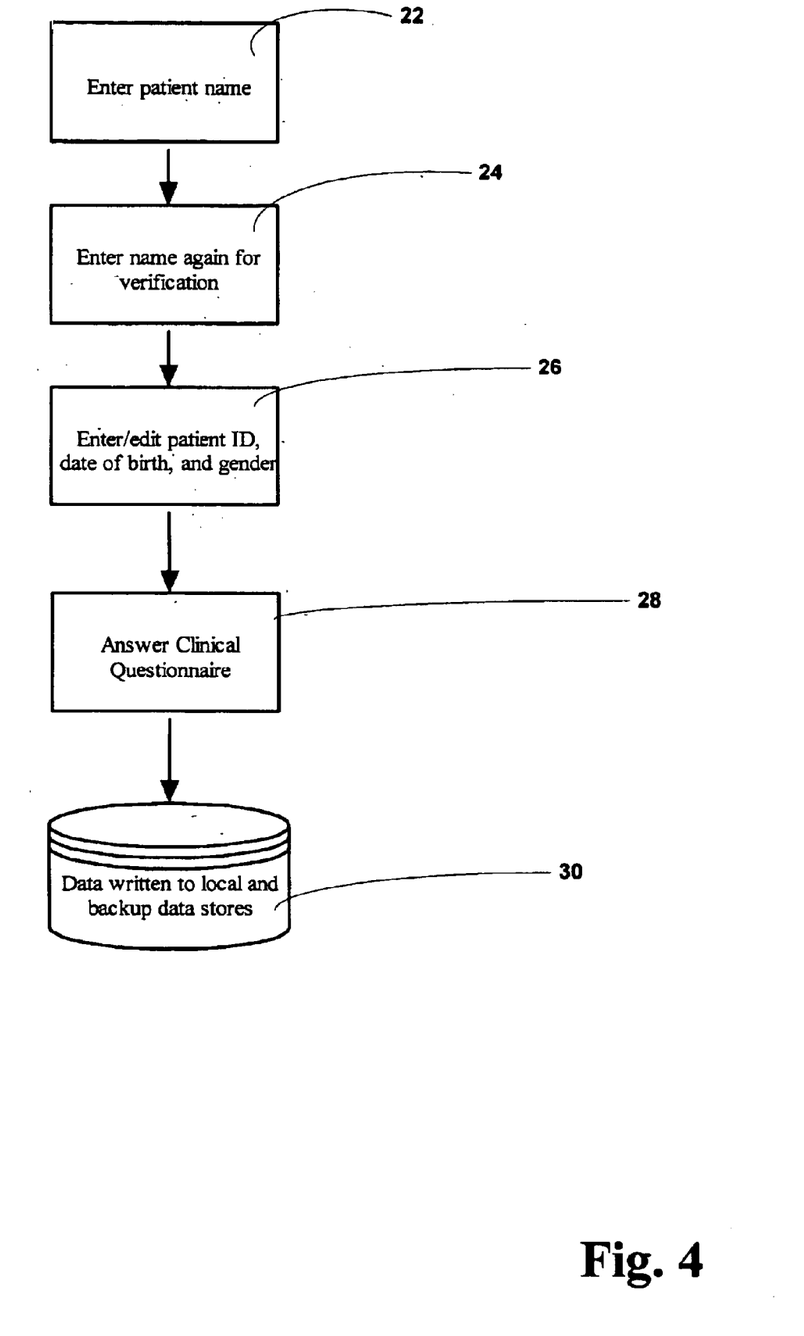
FIG. 4 is a flow diagram of the initialization steps of the system.

FIG. 4 shows the initialization steps in creating a new patient record at the remote testing unit 4, or accessing an existing patient record for purposes of answering the clinical questionnaire. In particular, remote testing unit 4 will cue the practitioner to enter a patient's name at step 22, again seek such entry at step 24 for verification. If it is a new patient, then the practitioner will be cued at step 26 to enter a patient ID, as well as other descriptive information like date of birth and gender. If it is a patient who is not new, then the patient identification and other information can be edited. Next, the clinical questionnaire is completed at step 28, and the results are written to a local and backup drive on remote testing unit 4. It should be appreciated that the clinical questionnaire, in this embodiment, comprises a series of questions with pull-down menu options for response. In alternative embodiments, the information is entered on a computer-readable or OCR recognizable sheet, and the information input via known forms of receiving such versions.

Figure 5:
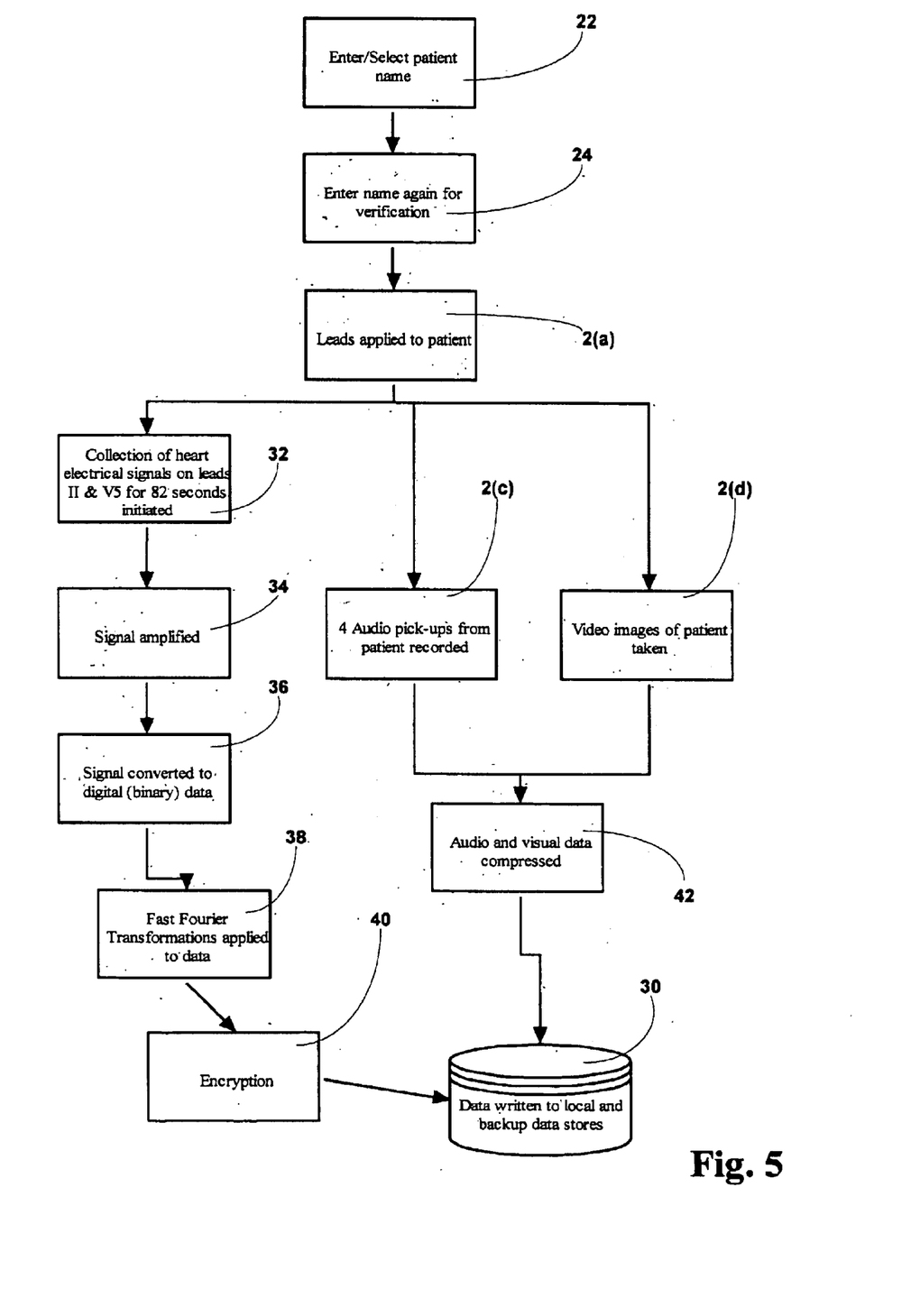
FIG. 5 is a flow diagram of the steps involved in collection of data by the remote testing unit portion of the subject invention.

FIG. 5 shows greater detail in the acquisition of patient-specific data In particular, as in FIG. 4, the patient's name is entered or selected (if pre-existing) at step 22, and re-entered at step 24 for verification. EKG leads are applied to the patient at step 2(*a*). Thereafter, the 82 second time period for collection of electrical signals from leads II and V5 is initiated at step 32, the signal is amplified at step 34, converted from analog to digital, binary form at step 36, FFT's applied at step 38, the resulting data is then encrypted at step 40 and written to local and backup data storage devices at step 30. Likewise, the audio information is recorded at step 2(*c*), video images of the patient are taken at step 2(*d*), the audio and video information is compressed at step 42, and this compressed information is also written to local and backup drives at step 30.

Figure 6:
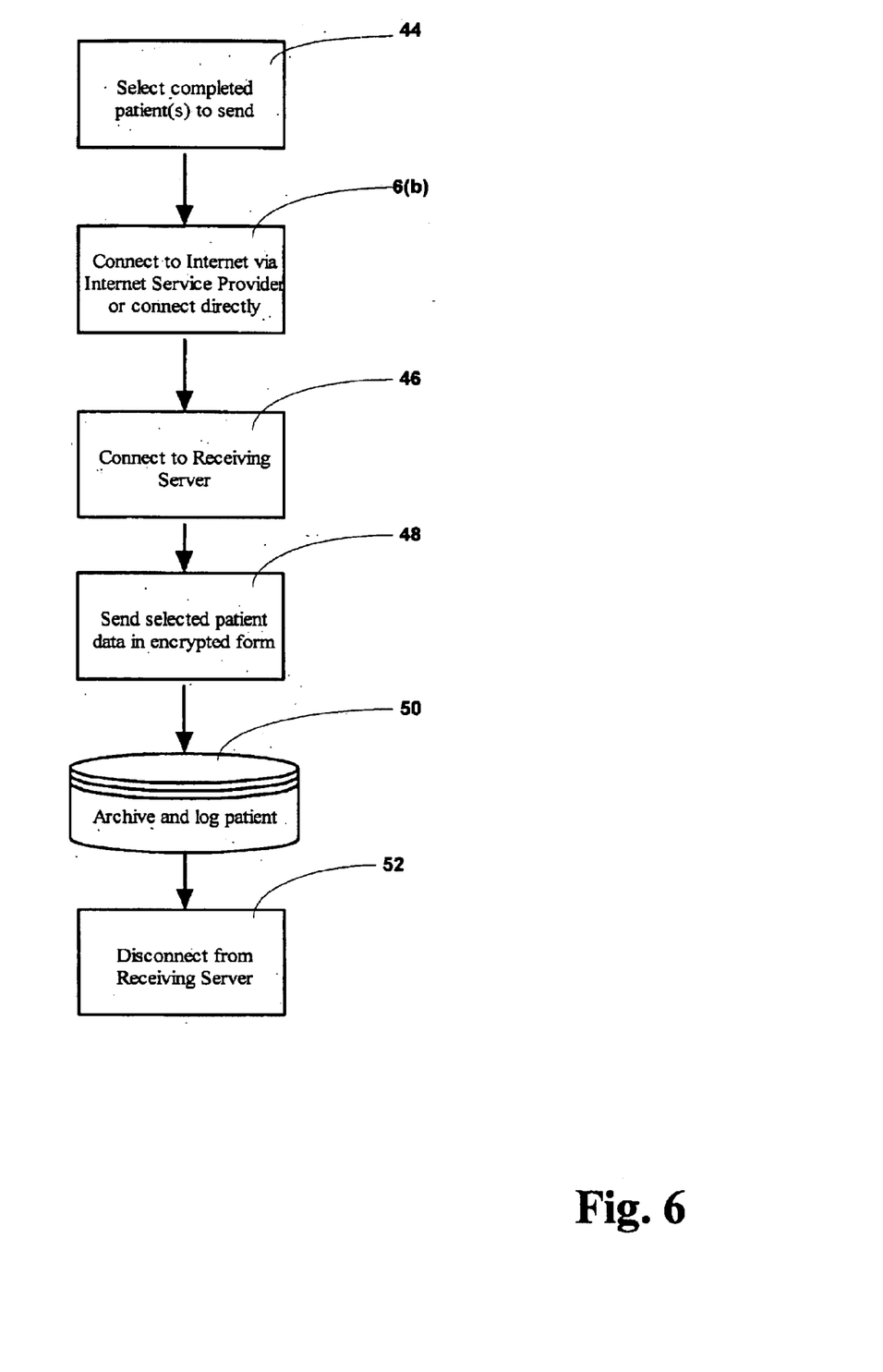
FIG. 6 is a flow diagram of the steps involved in the sending of data by the remote testing unit to the receiving server in accordance with the subject invention.

FIG. 6 shows greater detail of the process of sending the patient data to receiving server 8. In particular, the practitioner is cued to select the completed data from one or more patients. Connection to the Internet and to an ISP or via direct connection is then achieved at step 6(*b*). Connection via either medium to receiving server 8 is then achieved at step 46. Patient data in encrypted form is then sent from remote testing unit 4 to receiving server 8 at step 48. The data received is archived and logged at step 50. Upon completion of the transmission, the line is disconnected from receiving server 8 at step 52.

Figure 7:
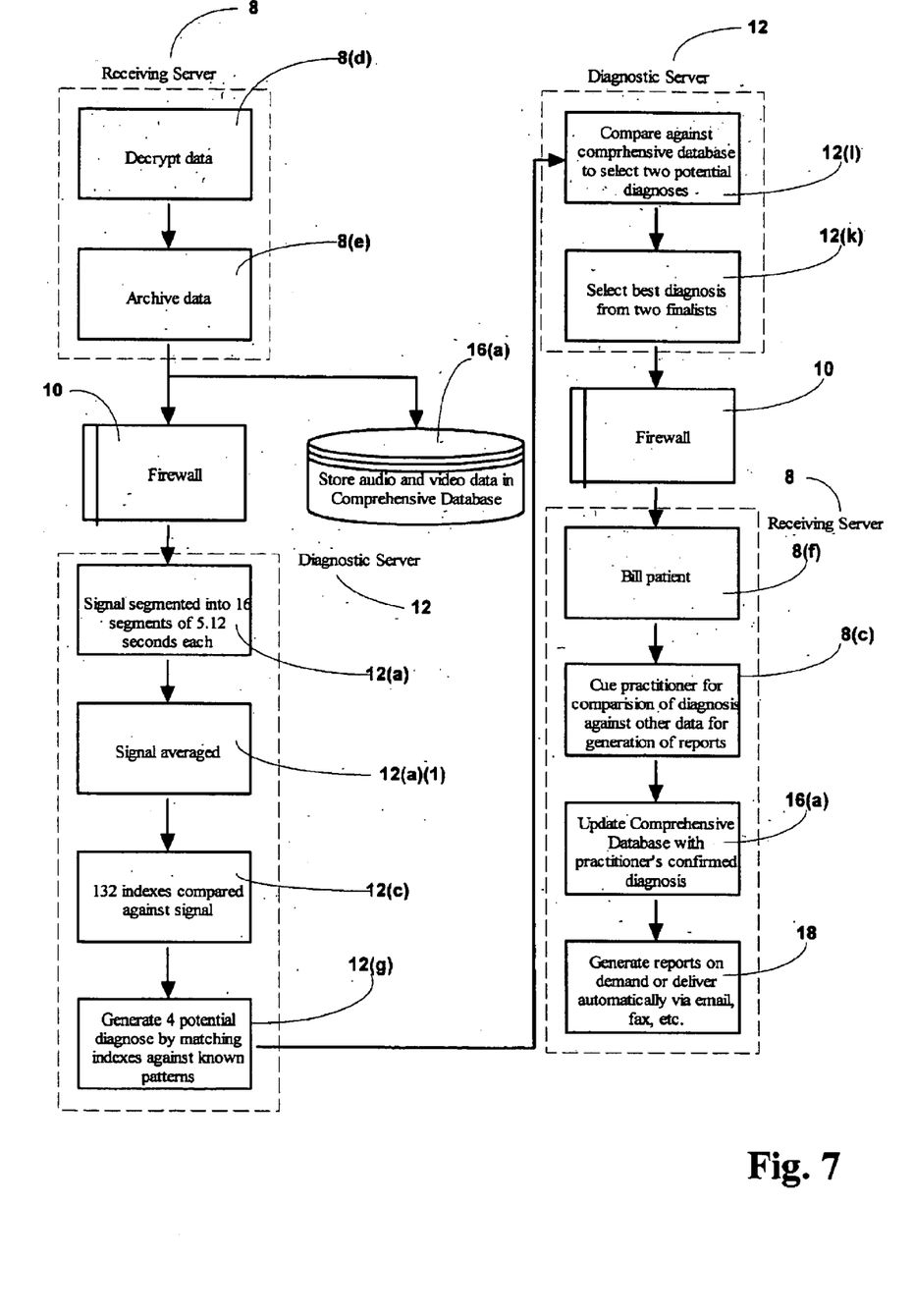
FIG. 7 is an overview of diagram of the connection between the receiving server, diagnostic server and the components therein, in accordance with a preferred embodiment of the subject invention.

FIG. 7 shows greater detail of the activities that occur at receiving server 8 and diagnostic server 12. In particular, receiving server 8 decrypts the received data at step 8(*d*), archives that data at step 8(*e*), and outputs that data for storage in comprehensive database 16, at step 16(*a*). Thereafter, the data is passed through firewall 10 into diagnostic server 12, where it is segmented at step 12(*a*), averaged at step 12(*a*)(*l*), 132 indexes compared against the signal at step 12(*c*), 4 potential diagnoses are generated by matching indexes against known patters at step 12(*g*), comparison is made against the comprehensive database to select two potential diagnoses at step 12(*i*), and the best diagnosis from the two potential diagnoses is selected at step 12(*k*). This best diagnosis is passed through firewall 10 back to receiving server 8. At this point the patient can be billed for the diagnostic service via step 8(*f*), the practitioner is cued via step 8(*c*), the comprehensive database updated at step 16(*a*), and reports generated at step 18.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

We claim:

1. A system for the detection of heart disease in a patient and providing at least one likely diagnosis from a plurality of potential diagnoses, comprising:

(a) data acquisition means for gathering data concerning the status of the patient's heart comprising application of EGK leads II and V5 to the patient, generating analog signals for each such lead, amplifying the generated signals, and converting the amplified signals to digital data;

(b) a remote testing unit for receiving the data gathered by the data acquisition means, including collecting the digital data, and for applying Fast Fourier Transforms ("FFT's") to said digital data to create transformed data having waveforms and for thereafter transmitting the acquired data including the transformed data;

(c) diagnostic means for receiving and analyzing the data transmitted by the remote testing unit, said diagnostic means comprising:

(1) mathematical translation means for translating the transformed data received from the remote testing unit into patient-specific patterns comprising a plurality of different graphical patterns representative of various states of the patient's heart, including performing the steps of:

(a) partitioning the waveforms of the transformed data into 16 segments of 5.12 seconds each at 100 data points per second and averaging the resultant signals;

(b) employing 6 transformations to the averaged signals;

(c) applying 132 indices to the transformed signals; and (d) identifying positive indices, integrating and creating said patient-specific patterns;

(2) a data base comprising graphical patterns representative of various states of a plurality of other patients' hearts from normal through disease states;

(3) comparing means for comparing said patient-specific patterns against the data base of graphical patterns and for recognizing those patterns in the data base more similar to said patient-specific patterns;

(4) diagnostic means for relating the recognized patterns to at least one likely diagnosis of the state of the patient's heart from the plurality of likely diagnoses; and (d) output means for outputting the at least one likely diagnosis.

2. The system of claim 1, wherein the data acquisition means comprises data gathering means selected from the group consisting of EKG leads, audio pickups, video images, text information containing clinical patient data, and combinations thereof.

3. The system of claim 2, wherein the data acquisition means further comprises an analog to digital converter for receiving analog information from the data gathering means and converting that data into a digital stream.

4. The system of claim 2, further comprising a comprehensive data base means connected to the system for storing audio, video, questionnaire information, diagnoses, graphs, reports and practitioner confirmation of diagnoses.

5. The system of claim 1, wherein the diagnostic means comprises a receiving server for performing the steps indicated in claim 1(*c*).

6. The system of claim 5, wherein the receiving server further comprises means for archiving the received data.

7. The system of claim 1, wherein the testing unit comprises an independent first computer, and the diagnostic means comprises an additional independent second computer.

8. The system of claim 7, wherein the first and second computers are connected to each other in an intranet fashion for the transmission of said data.

9. The system of claim 7, wherein the first and second computers are connected to each other via the Internet for the transmission of said data.

10. The system of claim 9, wherein the first and second computers comprise means for encrypting and de-encrypting the data that is transmitted between them.

11. The system of claim 9, wherein a firewall is provided between the first and second computers.

12. The system of claim 1, wherein the output means outputs the at least one likely diagnosis to the testing unit.

13. A method for the detection of heart disease in a patient, comprising the steps of:

(a) collecting analog information of at least EKG data from leads II and V5 concerning the status of the patient's heart;

(b) converting the analog information to digital data for receipt and processing;

(c) storing 82 seconds of EKG digital data;

(d) applying FFT's to the digital data;

(e) transferring the digital data to a receiving server;

(f) partitioning the digital data into signals of 16 segments of 5.12 seconds each at 100 data points per second;

(g) averaging the signals;

(h) employing transformations to the averaged signals;

(i) applying indices to the transformed signals;

(j) identifying positive indices, integrating and creating a patient-specific pattern;

(k) comparing the pattern against a data base of known conditions;

(l) determining at least one pattern in the data base of known conditions that compares in similarity to the patient-specific pattern;

(m) creating a likely diagnosis from the comparison; and (n) outputting the likely diagnosis.

14. The method of claim 13, wherein the analog information further includes information selected from the group consisting of clinical questionnaire data, audio pickups of heart audio information, and video images of the patient.

15. The method of claim 13, wherein the total number of transformations are 6 and the indices are 132.

16. The method of claim 13, further comprising the step of storing all digital data and analog information in a comprehensive data base.

* * * * *